United States Patent [19]

Miyagi et al.

[11] Patent Number: 5,438,975
[45] Date of Patent: Aug. 8, 1995

[54] DISTAL TIP OF ENDOSCOPE HAVING SPIRALLY COILED CONTROL WIRES

[75] Inventors: Kunihiko Miyagi; Toshio Chikama, both of Tokyo, Japan

[73] Assignee: Machida Endoscope Co., Ltd., Tokyo, Japan

[21] Appl. No.: 216,044

[22] Filed: Mar. 22, 1994

[30] Foreign Application Priority Data

| Mar. 24, 1993 | [JP] | Japan | 5-064918 |
| Mar. 24, 1993 | [JP] | Japan | 5-064919 |
| Mar. 24, 1993 | [JP] | Japan | 5-64920 |
| Mar. 24, 1993 | [JP] | Japan | 5-064921 |

[51] Int. Cl.⁶ ................................. A61B 1/005
[52] U.S. Cl. ................................. 600/109; 604/280; 600/141; 600/146
[58] Field of Search ................................. 128/4-10, 128/656-658, 772, 665; 604/280, 282, 283

[56] References Cited

U.S. PATENT DOCUMENTS

| 4,616,631 | 10/1986 | Takahashi | 128/6 |
| 4,742,817 | 5/1988 | Kawashima et al. | 128/4 |
| 5,108,368 | 4/1992 | Hammerslag et al. | 128/772 |
| 5,131,407 | 7/1992 | Ischinger et al. | 128/772 |
| 5,209,735 | 5/1993 | Lazarus | 128/657 X |
| 5,257,618 | 11/1993 | Kondo | 128/4 |

*Primary Examiner*—Richard J. Apley
*Assistant Examiner*—John P. Leubecker
*Attorney, Agent, or Firm*—Levisohn, Lerner, Berger & Langsam

[57] ABSTRACT

The distal ends of control wires of a distal tip deflection control mechanism are fixed to the distal tip of an endoscope. The distal ends of the control wires are spirally coiled up several times and form a cylinder, and the cylinder is fitted and fixed to the rear end or front end of the distal tip. In an alternate embodiment, the distal ends of the control wires are spirally coiled up several times and form a fitting body and the distal ends of an image guide, a charge coupled device (CCD), a light guide, or any other various kind of diagnostic tool or tube are fitted within the fitting body. In another version, the distal ends of the control wires are spirally coiled up several times around a bundle of distal ends of an image guide, a CCD, a light guide, or other various kinds of diagnostic tools or tubes, and the distal ends of the control wires and the bundle of distal ends of the other components are integrally fixed in the formed body.

11 Claims, 12 Drawing Sheets

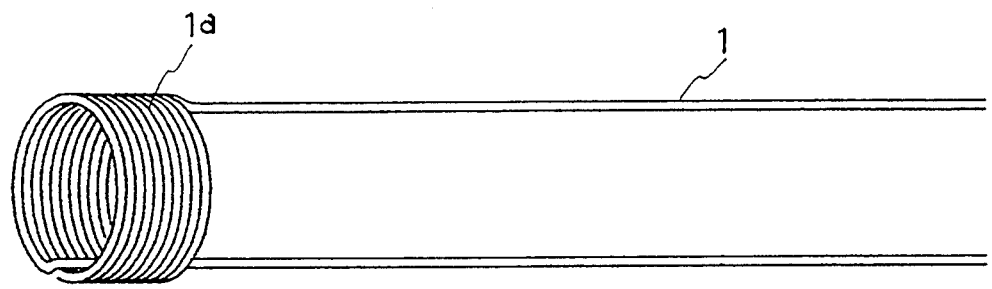
F I G . 1
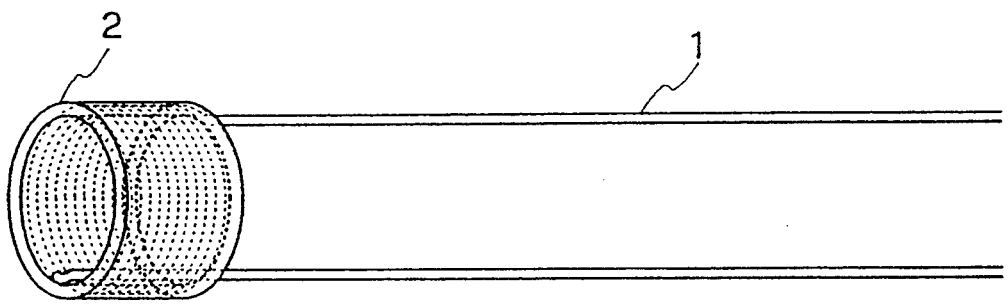
F I G . 2
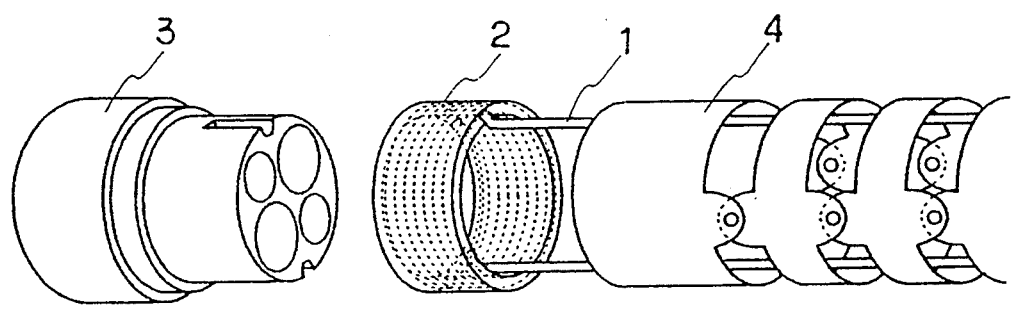
F I G . 3

DISTAL TIP OF ENDOSCOPE HAVING SPIRALLY COILED CONTROL WIRES

FIELD OF THE INVENTION

The present invention relates to a distal tip of an endoscope (including a catheter) having the ends of the control wires of the distal tip deflection control mechanism fixed.

BACKGROUND OF THE INVENTION

Modern endoscopes have a distal tip deflection control mechanism for facilitating guided advancing within the human body cavity and for changing the facing direction of the objective lens of the distal tip according to the position of the object sought to be observed. Such distal tip deflection control mechanism includes control wires whose distal ends are fixed to the distal tip of the endoscope. The distal tip is thus operated by controlling the proximal end of the control wires at the proximal housing of the endoscope.

The distal ends of the control wires require that they be firmly fixed to the distal tip of the endoscope so that they cannot be easily broken, and on the other hand, the mechanism for holding the wires at the tip must not increase the diameter of the distal tip. Japanese Utility Model Publication No. 3-52483 (hereinafter "the 3-52483 reference"), Japanese Patent Publication Nos. 3-72291 (hereinafter "the 3-72291 reference") and 4-10327 (hereinafter "the 4-10327 reference") are the prior art attempts to satisfy these requirements.

In the 3-52483 reference, as shown in FIG. 30 hereof, a stopper 7 is fixed to the distal ends of control wires 6 (only one is shown), and the stopper 7 is fitted and fixed within a groove 9 formed on the outer circumference of the distal tip 8. An end segment of the tubular segments of the endoscope (shown in phantom) is fitted to the rear end of the distal tip and it covers and secures the circumference of the stoppers 7 within the groove 9.

In the 3-72291 reference, as shown in FIG. 31 hereof, a stopper projection 11, laterally directed, is formed at the distal end of a control wire 10, and the distal end of the control wire 10 is fitted and fixed within a groove 13 formed on the outer circumference of the distal tip 12. An end segment of the tubular segments of the endoscope (not shown) is fitted to the rear end of the distal tip and the stopper projection 11 is hooked over the top end of the end segment.

In the 4-10327 reference, as shown in FIG. 32 hereof, grooves 15a and 15b are hollowed out of a distal tip 14. The distal ends of the control wires 16a and 16b are secured in the grooves 15a and 15b, respectively, and are secured in place by filling up the grooves 15a and 15b with wire fixing material 17.

SUMMARY OF THE INVENTION

This invention describes a distal tip of an endoscope in which the distal ends of the control wires of the distal tip deflection control mechanism are fixed and in which the distal ends of the control wires are spirally coiled to form a cylinder. This cylinder is fitted and fixed to the rear or front end of the distal tip.

This invention also describes a distal tip of an endoscope in which the distal ends of the control wires of the distal tip deflection control mechanism are spirally coiled up several times to form a fitting body. Distal ends of various diagnostic tools of the endoscope, e.g., an image guide, a CCD, a light guide, and the like are fitted and fixed within the formed fitting body. The distal ends of the image guide, a CCD, a light guide, other kinds of diagnostic tools and the like and the fitting body are thus held together as a unitary body, and this integral body forms a distal tip.

This invention also describes a distal tip of an endoscope in which the distal ends of the control wires of the distal tip deflection control mechanism are spirally coiled, several times around a bundle of the distal ends of an image guide, a CCD, a light guide, and/or other kinds of diagnostic tools. The distal ends of the control wires and the bundle of distal ends of the other diagnostic tools, e.g., the image guide, a CCD, a light guide, are then joined as one united body, and this united body forms a distal tip.

It is an object of the present invention to avoid increasing the diameter of the mechanism for securing the distal ends of the control wires to the tip of the endoscope, so as to maintain the slender profile of the endoscope. The profile is a very important factor in the use and success of this apparatus.

It is a further object of the present invention to obtain a firm securement of the distal ends of the control wires to the tip of the endoscope.

It is a further object of the present invention to provide an endoscope which can use thinner control wires, so as to further slenderize the shaft portion of the endoscope.

It is a further object of the present invention to minimize the number of parts of the endoscope, and also to simplify the securement of the control wires.

It is a further object of the present invention to provide an endoscope which can use stainless steel control wires. Prior to the present invention, that has not been possible.

It is a further object of the present invention to provide an endoscope which can allow for selective replacement of the control wires without taking the endoscope entirely apart.

It is a further object of the present invention to form a distal tip of an endoscope at the same time as the distal ends of the control wires are fixed to the distal tip, for minimizing the number of parts of the endoscope as well as for slenderizing the distal tip of the endoscope.

BRIEF DESCRIPTION OF THE DRAWINGS

FIG. 1 is a perspective view showing the spirally coiled portion of the control wires;

FIG. 2 is a perspective view showing the cylinder in phantom formed from the spirally coiled control wires shown in FIG. 1;

FIG. 30 is a perspective view showing an example of the prior art;

FIG. 31 is a perspective view showing another example of the prior art; and

DETAILED DESCRIPTION OF THE PREFERRED EMBODIMENTS AND THE DRAWINGS The Preferred Embodiment The preferred embodiment of the distal tip of the present invention will now be described. In FIGS. 1 and 2, the reference numeral 1 designates control wires of a distal tip deflection control mechanism. In the present invention, the distal ends of control wires 1 are spirally coiled up several times as shown in FIG. 1, and this spirally coiled portion 1a of the control wires 1 is formed into a cylinder 2 as shown in FIG. 2.

Figure 11:
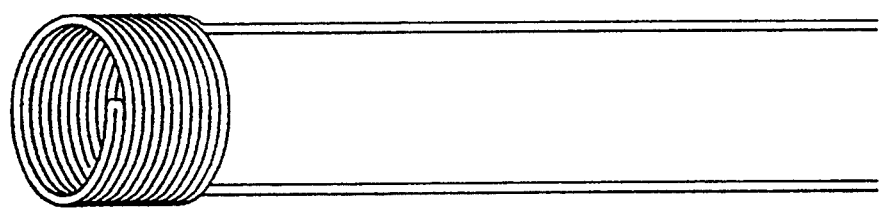
FIG. 11 is a perspective view showing another version of the spirally coiled portion of the control wires.
Figure 12:
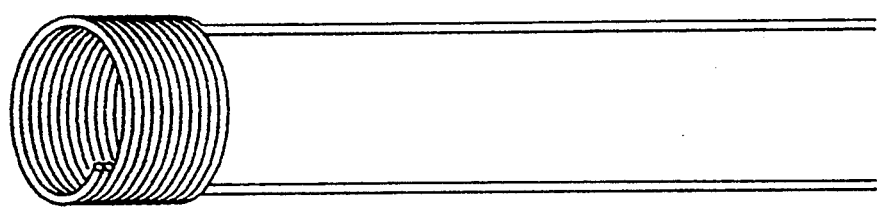
FIG. 12 is a perspective view showing another example of the spirally coiled portion of the control wires.
Figure 13:
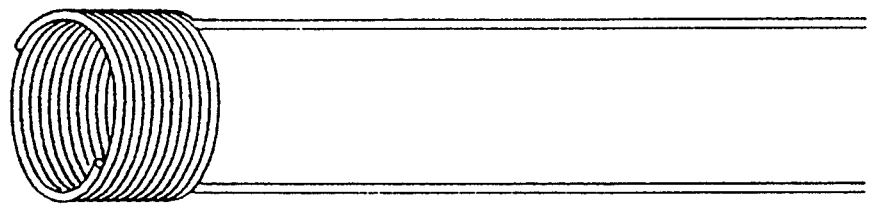
FIG. 13 is a perspective view showing another example of the spirally coiled portion of the control wires.
Figure 14:
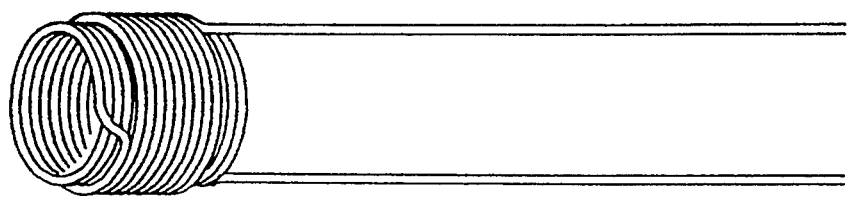
FIG. 14 is a perspective view showing another example of the spirally coiled portion of the control wires.

The two control wires 1 of this embodiment are formed from a single wire having a central portion coiled up several times to form the spirally coiled portion 1a. However, there are many ways for forming the spirally coiled portion 1a. For example, as shown in FIG. 11, the two sides of the single wire may be bundled and coiled up in a first direction, and then reversed at its distal portion, or, as shown in FIG. 12, two wires 1 may be bundled and coiled up in a single direction. Further, the spiral wires may be coiled up as shown in FIG. 13, or, the spirally coiled portion 1a may be coiled up in layers as shown in FIG. 14.

The material for the control wire 1 may be metal and stainless steel is preferred. Artificial fiber or natural fiber can also be used. In the spirally coiled portion 1a, adjacent coil sections may touch or be spaced from each other.

The method for keeping the cylindrical shape of cylinder 2 depends upon the material of the control wire 1. The cylinder 2 of a predetermined diameter is formed by molding, adhesive, soldering, wax-adhesive or a laser welding process applied to the spirally coiled portion (1a). It is also possible to form the cylindrical shape of cylinder 2 by first forming a solid cylinder by a molding process and then hollowing out the center of the cylinder.

Figure 15:
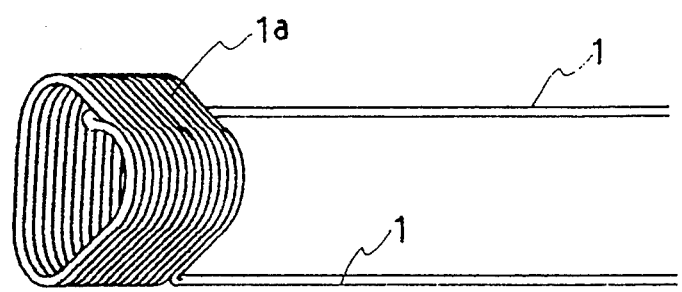
FIG. 15 is a perspective view showing another example of the spirally coiled portion of the control wires.

There is no necessity for forming the cylinder 2 with both ends having the same diameter as shown in FIG. 2, and it can be, e.g., a frustoconical section with each end having a different diameter, or even an angular shape as shown in FIG. 15, a flat shape, etc., as desired.

Figure 4:
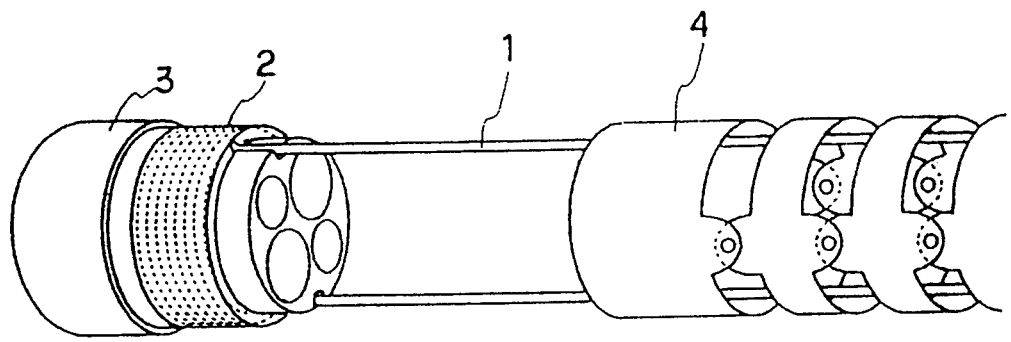
FIG. 4 is a perspective view showing the first embodiment of the invention after further assembly.
Figure 3:
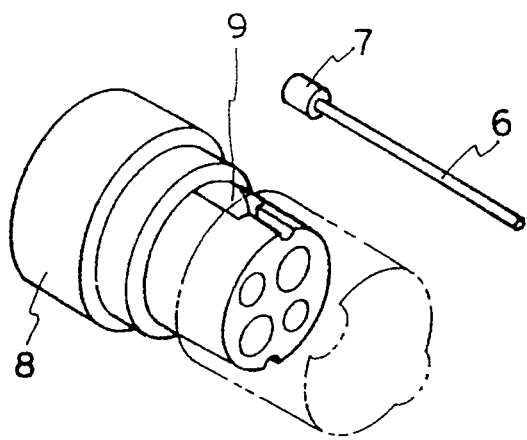
FIG. 3 is a perspective view showing the first embodiment of the invention during initial assembly and using the coil cylinder of FIGS. 1 and 2.
Figure 3:
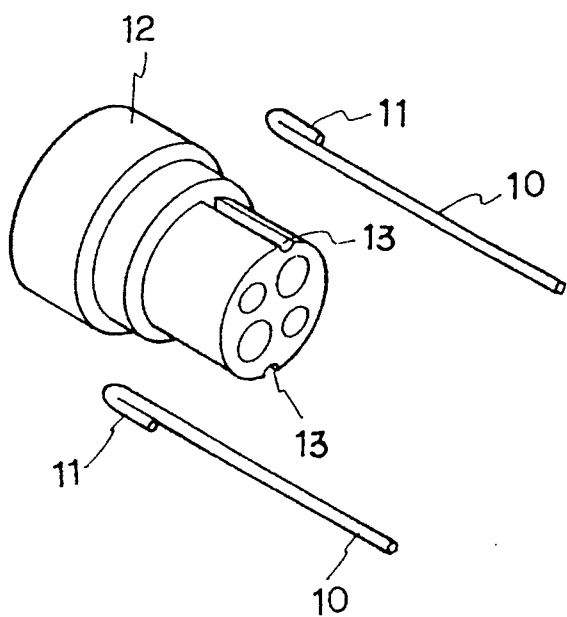
Figure 32:
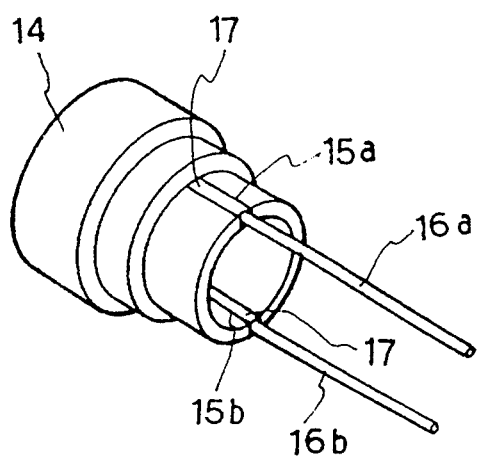
FIG. 32 is a perspective view showing another example of prior art.

A cylinder 2 is fitted to the outer circumference of the rear end of a distal tip 3 of the deflectable section of the endoscope, as shown in FIG. 3, and the cylinder 2 and the distal tip 3 are unified by molding, adhesive, soldering or another similar process. The unified device is shown in FIG. 4.

Figure 5:
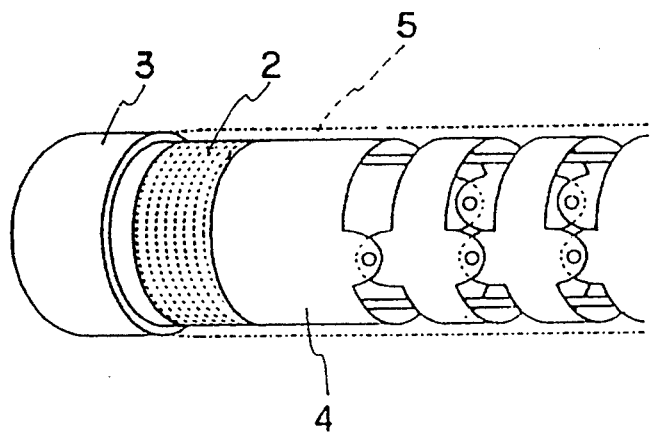
FIG. 5 is a perspective view showing the first embodiment of the invention after further assembly.
Figure 6:
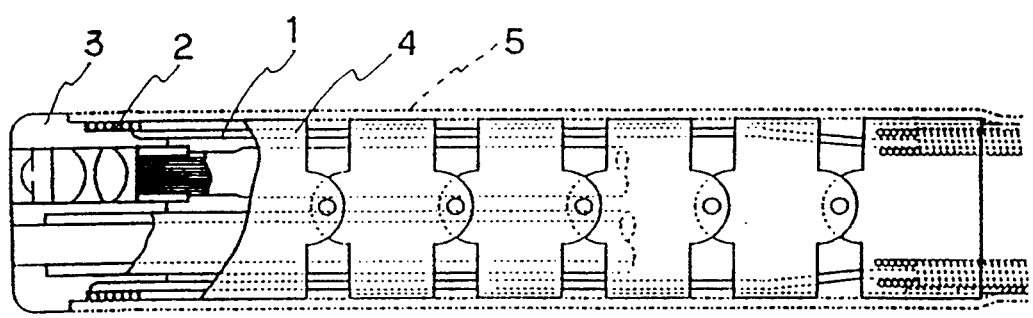
FIG. 6 is a cross-sectional side view, partially cutaway, and showing the first embodiment of the invention along with other components of the endoscope, after assembly.

After unifying the cylinder 2 and the distal tip 3, the end segment 4 of a plurality of tubular segments is fitted to the rear end of the distal tip 3 as shown in FIG. 5 and FIG. 6 and the distal tip 3 and the flexible shaft of the endoscope are thus joined together.

The proximal ends of the control wires 1 extend to the proximal end of the endoscope and are connected to a distal tip deflection control mechanism which is not shown in the figures and is not a part of the present invention.

An outer cover 5 (See FIGS. 5 and 6, showing it in phantom) covers the deflectable section including the distal tip 3 and the consecutive flexible shaft members, as shown in FIG. 6.

Figure 7:
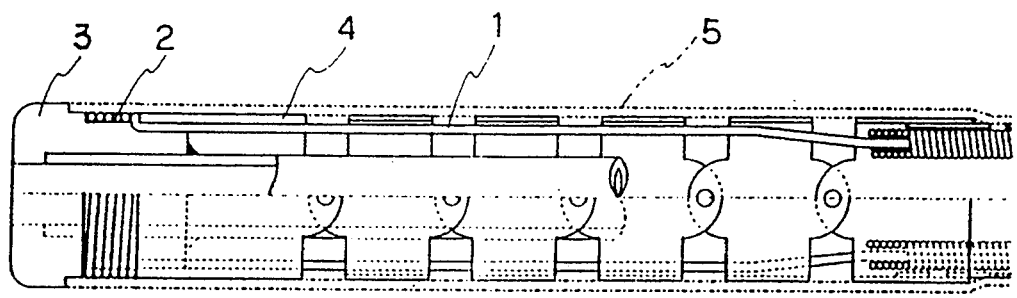
FIG. 7 is a cross-sectional side view, partially cut away, and showing a second version of the first embodiment of the invention.

The present invention has been explained as to endoscopes; however, the construction of the present invention would be adapted for use with catheters. As shown in FIG. 7, in a catheter, the cylinder 2 is fitted to the outer circumference of the rear end of a distal tip of the catheter, and the cylinder 2 and the distal tip are unified by molding, adhesion, soldering or a similar process. The proximal ends of these control wires 1 are extended to the proximal end of the catheter, and are connected to the distal tip deflection controls of the catheter which are not shown in the Figures.

In this manner, in the present invention, the distal ends of the control wires are fixed to the distal tip of the endoscope/catheter within a certain small area, simply by fitting the cylinder of the tip of a predetermined diameter, with a formed coil made from the distal ends of the control wires. Accordingly, the present invention avoids thickening of the distal ends of the control wires at the point of their being fixed to the end of the device, and maintains the overall small thickness of the shaft portion of the endoscope/catheter. This, as mentioned, is a particularly important factor in the success of these apparatus.

Also, in the present invention, since the distal ends of the control wires are fixed to the distal tip of the endoscope/catheter, within a certain area, the securement is sure and will not be easily broken, even if the control wires are subject to strong tension or stress. Therefore, according to the present invention, thinner control wires are possible, and thus, the shaft portion of the endoscope/catheter can be even further slenderized.

Furthermore, in the present invention, since the cylinder is simply fitted and fixed to the distal tip of the endoscope/catheter, no other parts are necessary. This, too, simplifies the mechanism.

Still further, use of the present invention allows a different method for fixing the control wires to be available, other than soldering. Therefore, according to the present invention, it is now possible to use stainless steel wires. The durability of the control wires is thus improved.

An Alternate Embodiment

Another embodiment of the distal tip of the present invention will now be described.

Figure 8:
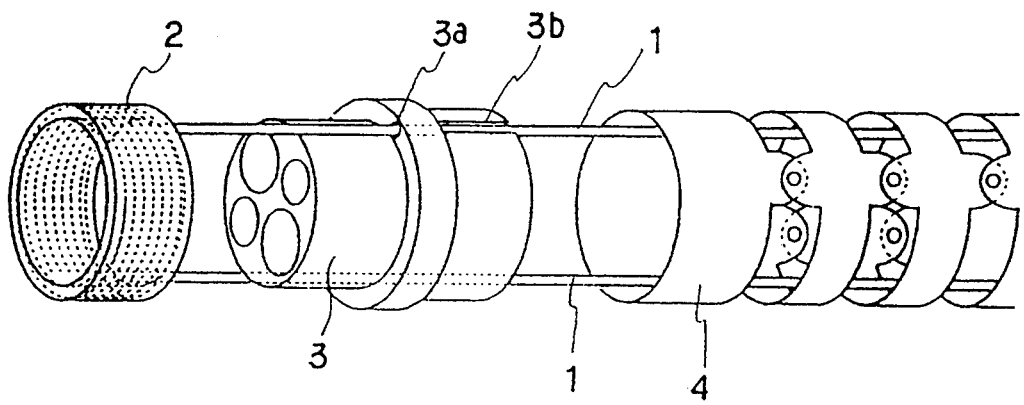
FIG. 8 is an exploded perspective view showing the second embodiment of the invention.
Figure 9:
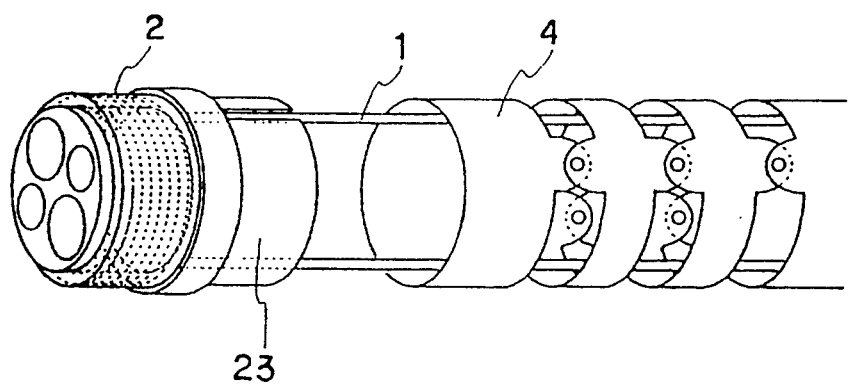
FIG. 9 is a perspective view showing the second embodiment of the invention during initial assembly.

The structure of the cylinder 2 is the same as was described above. The cylinder 2 is fitted to the outer circumference of the front end of a distal tip 23 of the deflectable section of the endoscope as shown in FIGS. 8 and 9, and the cylinder 2 and the distal tip 23 are joined again by molding, adhesive, soldering or a similar process as shown in FIG. 9.

After the unification, joining of the cylinder 2 and the distal tip 3, the end segment 4 of the tubular segments is fitted to the rear end of the distal tip 23, and the distal tip 23 and the flexible shaft of the endoscope are unified/joined, with the following tubular segments secured in order.

The proximal ends of the control wires 1 are extended to the proximal end of the endoscope, and are connected to the distal tip deflection controls which are not shown in the Figures.

An outer cover 5 (see FIG. 10) covers the deflectable section including the distal tip 23 and the flexible shaft segments.

The control wires 1 of this embodiment of the present invention can be replaced without taking the endoscope apart. That is, a new set of control wires 1 can be fitted and replaced by connecting their proximal ends to the distal ends of old control wires 1 and drawing out the old control wires 1 from their proximal side.

Figure 10:
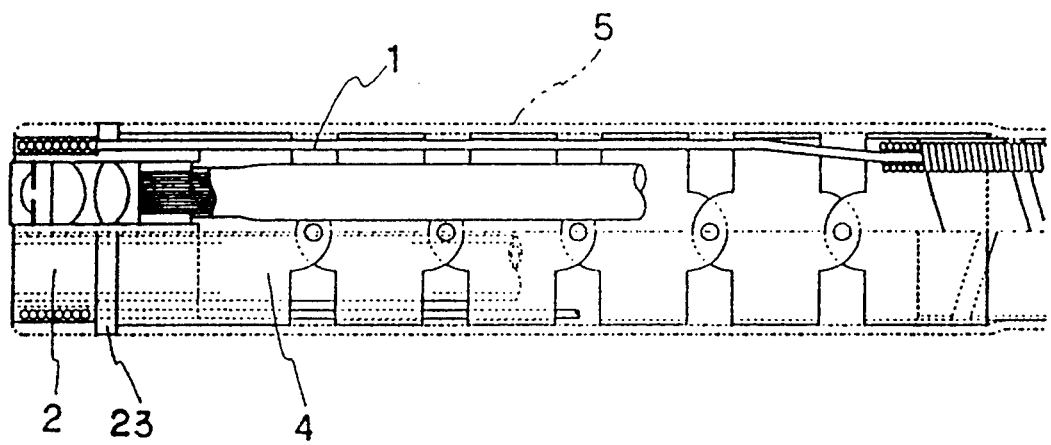
FIG. 10 is a partial cross-sectional side view, showing another version of the second embodiment of the invention.

The present invention has been explained as to endoscopes; however, the construction of the present invention is equally suited for use with catheters. As shown in FIG. 10, a catheter has a cylinder 2 located at the far end, about the circumference of a distal tip of the catheter. The cylinder 2 and the distal tip are joined by molding, adhesive, soldering or a similar process. The proximal ends of these control wires 1 are extended to the proximal end of the catheter, and are connected to the distal tip deflection controls which are not shown in the Figures.

In this manner, in the present invention, the distal ends of the control wires are fixed to the distal tip of the endoscope/catheter within a certain area, simply by fitting the coiled cylinder of a certain diameter, formed by coiling up the distal ends of the control wires. Accordingly, the present invention avoids increasing the thickness of the portion of the distal ends of the control wires used for holding the same, and results in a slender shaft portion of the endoscope catheter. That is particularly important for the success of this apparatus.

Also, in the present invention, since the coiled cylinder is fitted from the front end of the distal tip of the endoscope/catheter, replacement of the control wires without taking the endoscope apart is possible.

Also, in the present invention, since the distal ends of the control wires are fixed to the distal tip of the endoscope/catheter within a certain area, their securement is sure and they will not easily be broken, even if the control wires are subject to strong tension or stress. Therefore, according to the present invention, thinner control wires can be used, and the shaft portion of the endoscope/catheter can be slenderized.

Furthermore, in the present invention, since the coil is simply fitted and fixed to the distal tip of the endoscope/catheter, no other parts are necessary.

Still furthermore, in the present invention, one can choose a variety of methods for fitting and securing the control wires and, therefore, soldering can be avoided. Therefore, according to the present invention, the present invention allows the use of stainless steel wires which had not previously been possible. The durability of the wires is thus improved.

The Third Embodiment

Figure 17:
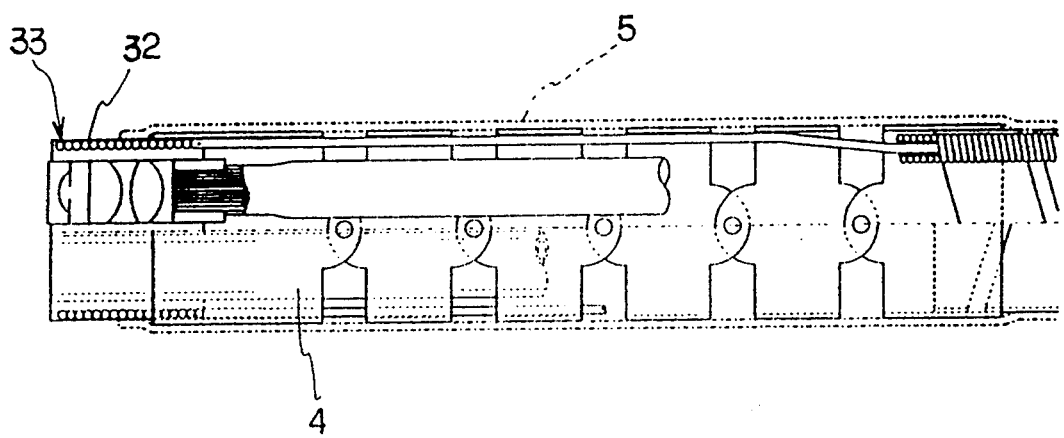
FIG. 17 is a partial cross-sectional side view showing a third embodiment of the invention.

Versions of the distal tip of the third embodiment of the invention will now be described. The structure of the fitting body 32 (the coil of control wires) is the same as the cylinder 2 described above. Distal ends of an image guide, a CCD, a light guide, and various other kinds of diagnostic tools in the form of tubes and the like, are fitted in the fitting body 32, and by unifying the fitting body 32 and the distal ends of said tubes (by molding, adhesive and the like, as shown in FIG. 17) a distal tip 33 of an endoscope results. The result is an integral unit formed at the same time as fixing of the distal ends of the control wires 1 is performed.

Figure 18:
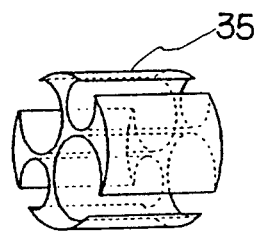
FIG. 18 is a perspective view showing a spacer element used in the third embodiment.

Further, when precise positioning of the distal ends of the image guide, a CCD, a light guide, various kinds of diagnostic tools in the form of tubes and the like is desired, a spacer element 35 which has channels or guide grooves for holding each of the distal ends of the diagnostic tools, e.g., an image guide, a CCD, a light guide, various other kinds of tubes and the like, can be used, as shown in FIG. 18.

After the distal tip 33 is formed, the end segment 4 of the tubular or short pipe segments is fitted to the rear end of the distal tip 33 as shown in FIG. 17.

The proximal ends of the control wires 1 extend to the proximal end of the endoscope and are connected to distal tip deflection controls, which are not shown in the Figures.

An outer cover 5 covers the deflectable section including the distal tip 33 and the consecutive flexible shaft members as shown in FIG. 17.

In this manner, in the present invention, the distal ends of the control wires are fixed to the distal tip of the endoscope/catheter within a certain area, simply by fitting and securing the distal ends of diagnostic tools, e.g., an image guide, a CCD, a light guide, and various other kinds of tubes and the like, all within the fitting body of a certain diameter which is formed by coiling up the distal ends of the control wires.

Figure 19:
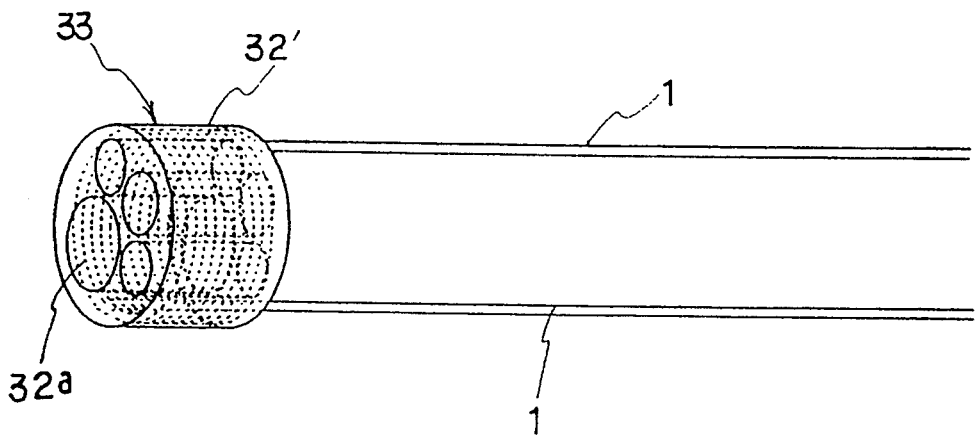
FIG. 19 is a perspective view showing another version of the third embodiment of the invention.
Figure 20:
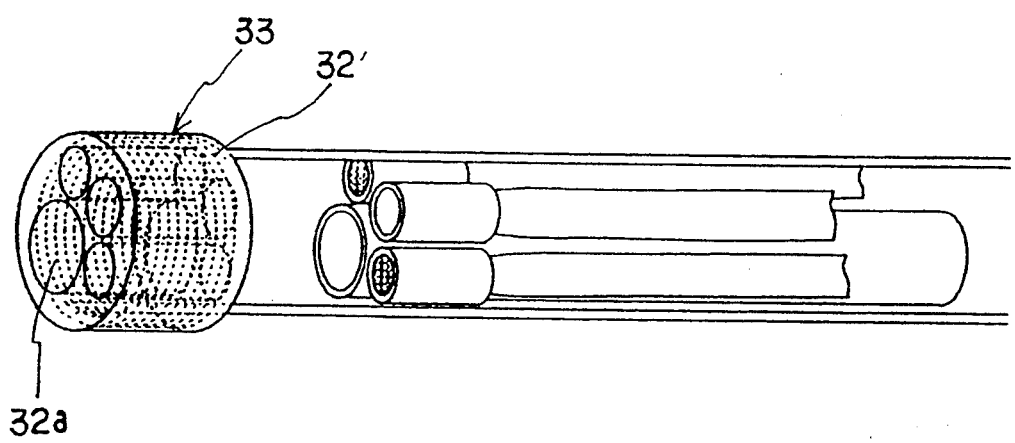
FIG. 20 is a perspective view showing more of the components of the version of the third embodiment of the invention shown in FIG. 19.

In the embodiment shown in FIGS. 19 and 20, the fitting body 32, formed from the spiral cylinder of control wires is not a smooth-walled cylinder, but follows the contour of joined-together pipes, having holes 32a passing through, along the longitudinal axis. Such fitting body 32 may be formed from a solid column, by a molding process and the like, followed by a hollowing out or drilling of the holes 32a passing through the axis of the column. Further, it may be formed by applying a snap flash molding, so that the fitting body 32 and the holes 32a can be formed at one time. Then, as shown in FIG. 20, the distal tip 33 is constructed by fitting and fixing the distal ends of an image guide, a CCD, a light guide, various other kinds of diagnostic tools in the form of tubes and the like, within their own aligned holes 32a.

According to this structure, a precise positioning of the distal ends of an image guide, a CCD, a light guide, various other kinds of diagnostic tools in the form of tubes and the like is made possible by first positioning the holes 32a precisely.

Figure 21:
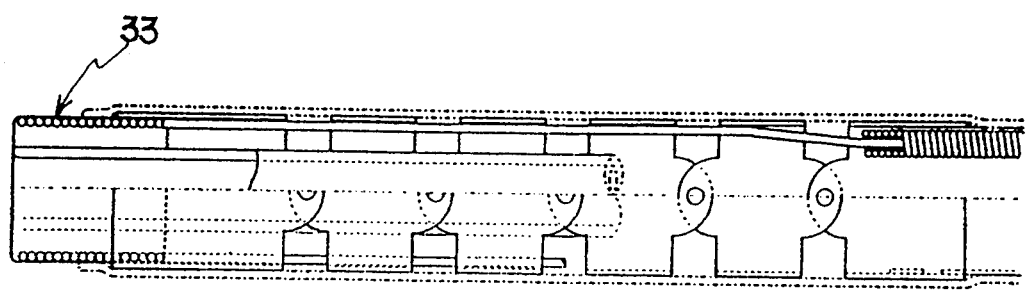
FIG. 21 is a perspective view showing another version of the third embodiment of the invention.

The present embodiment is described as to endoscopes, however, the construction of the present invention could be employed for catheters, too. As shown in FIG. 21, a catheter has the distal end of the tube of the catheter fitted with the fitting body, and by unifying the fitting body 32 and the distal ends of these tubes by molding, adhesive and the like, a distal tip 33 of the catheter is formed at the same time as securing of the distal ends of the control wires 1. The proximal ends of these control wires 1 are extended to the proximal end of the catheter, and are connected to the distal tip deflection controls which are not shown in the Figures.

In this manner, in the present invention, the distal tip of an endoscope can be formed at the same time as the distal ends of the control wires are fixed to the distal tip, simply by fitting and fixing the distal ends of an image guide, a CCD, a light guide, various kinds of diagnostic tools in the form of tubes and the like, to the fitting body which is formed by coiling up the control wires. The invention can avoid small and precise parts of metal/synthetic resin for the distal tip, and results in a slender profile of the distal tip of the endoscope. Simplifying of the fixing of the control wires also results. Also, the invention avoids thickening of the fixing portion of the distal ends of the control wires, and slenderizes the shaft portion of the endoscope/catheter.

Also, in the present invention, since the distal ends of the control wires are fixed to the distal tip of the endoscope/catheter within a certain area, the fixation of them is sure and will not be broken even if the control wires are subject to strong tension or stress. Therefore, according to the present invention, it is possible to use thinner control wires, and the shaft portion of the endoscope/catheter can be further slenderized.

Furthermore, in the present invention, since the cylinder is simply fitted and fixed to the distal tip of the endoscope/catheter, no other parts are necessary.

Still furthermore, in the present invention, a greater variety of choice in the method for fixing the control wires is present and soldering can be avoided. Therefore, according to the present invention, it is now possible to use stainless steel wires. The durability of these wires is improved over the prior art.

Fourth Embodiment

Figure 22:
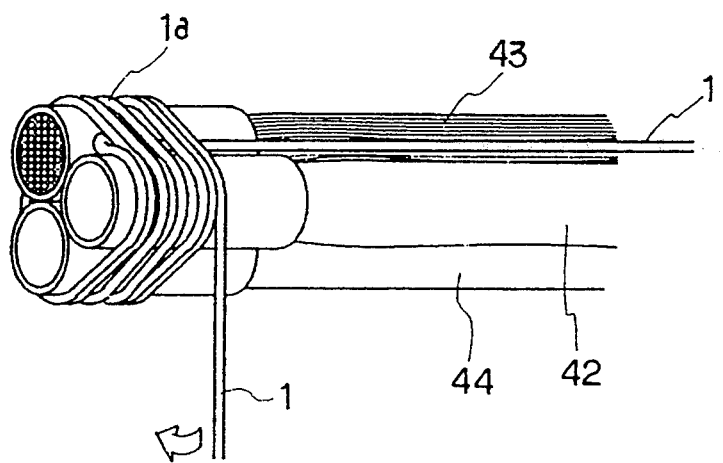
FIG. 22 is a perspective view showing the fourth embodiment of the invention.
Figure 23:
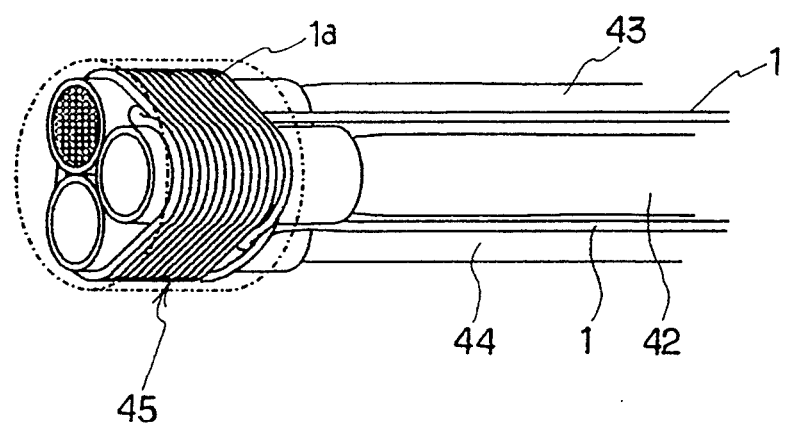
FIG. 23 is a perspective view showing a second version of the fourth embodiment of the invention.

The fourth embodiment of the distal tip of the present invention will now be described. In FIGS. 22 and 23, the reference numeral 1 designates control wires of a distal tip deflection control mechanism. In the present invention, the distal ends of control wires 1 are spirally coiled several times around the distal ends of diagnostic tools in the form of an image guide, a CCD, a light guide, various other kinds of tubes and the like, which are then fixed to each other with adhesive and bundled up. By unifying this spirally coiled portion 1a of the control wires and the distal ends of said tubes, a distal tip 45 of an endoscope is formed at the same time as the fixing of the distal ends of control wires 1. The method for fixing the spirally coiled portion 1a depends upon the material of the control wire 1, that is, molding, adhesion, soldering, wax-adhesion or laser welding processes can be used. The openings formed on the outer surface can be sealed with adhesive, sealing parts and the like, if necessary.

In the embodiment shown in FIG. 23, a harder distal tip 45 is provided by unifying the spirally coiled portion 1a and the distal end of the tubes, all by molding.

Figure 24:
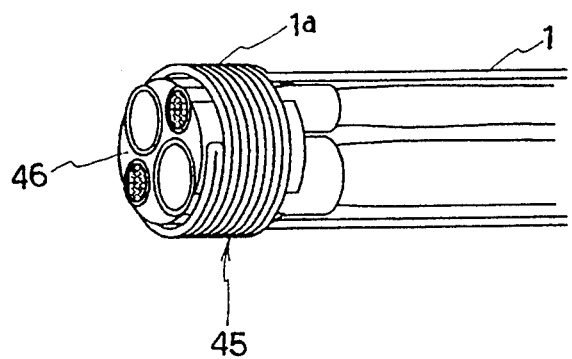
FIG. 24 is a perspective view showing another version of the fourth embodiment of the invention.

Further, when precise positioning of distal ends of an image guide, a CCD, a light guide, various other kinds of diagnostic tools in the form of tubes and the like, or uniformity of the shape of the distal tip 45 are desired, a spacer 35 which has guide grooves for fitting the diagnostic tools e.g., an image guide, a CCD, a light guide, various other kinds of tubes and the like, as shown in FIG. 18 may be used as shown in FIG. 24. The spacer 35 can be used as the spacer and the mechanism for sealing between tools.

Figure 25:
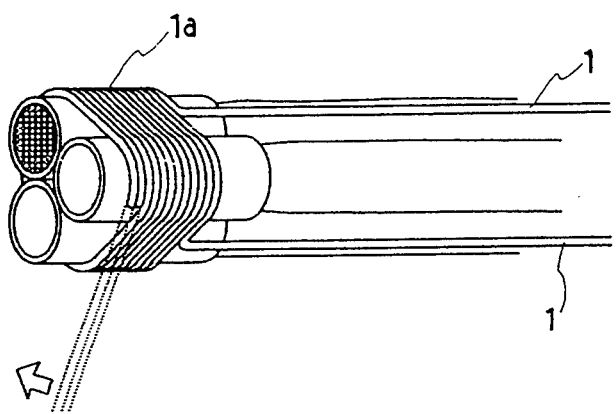
FIG. 25 is a perspective view showing the fourth version of the fourth embodiment of the invention.

The two control wires 1 of the above-described embodiment are formed from a single wire with which a central portion is coiled up several times to form the spirally coiled portion 1a. However, there are many ways for forming the spirally coiled portion 1a. For example, as shown in FIG. 24, the two sides of the single wire may be bundled and coiled up in opposite directions, or, as shown in FIG. 25, two wires 1 may be bundled and coiled up in one direction. Further, the plural wires may be coiled up as shown in FIG. 13, or, the spirally coiled portion 1a may be coiled up in layers as shown in FIG. 14.

The material of the control wires 1 may be metal, for example, stainless steel, artificial fiber or natural fiber. In the spirally coiled portion 1a, the adjacent coils may touch or be spaced apart from each other.

Figure 26:
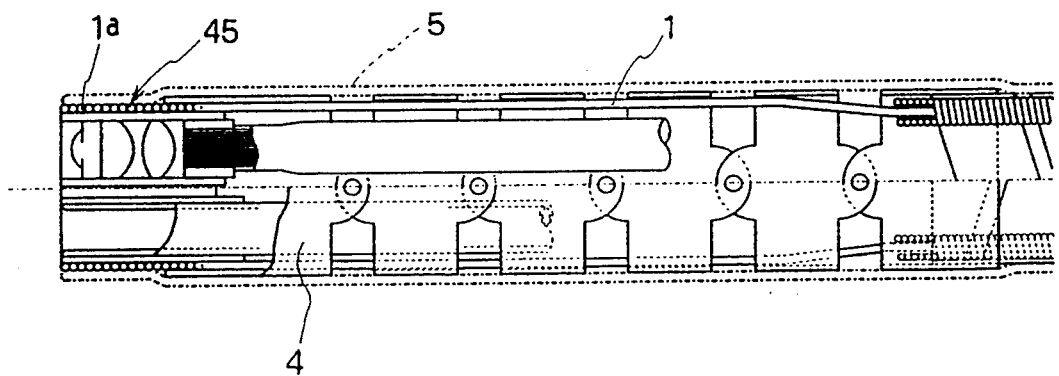
FIG. 26 is a partial cross-sectional side view showing the first version of the fourth embodiment of the invention as seen in FIG. 22.

After the distal tip 45 is formed, the distal end segment 4 of the tubular segments is fitted to the rear end of the distal tip 45 as shown in FIG. 26 and the distal tip 45 and the flexible shaft of the endoscope sequentially assembled.

The proximal ends of these control wires 1 are extended to the proximal end of the endoscope, and are connected to distal tip deflection controls which are not shown in the Figures.

An outer cover 5 covers the deflectable section including the distal tip 35 and the consecutive flexible shaft segments as shown in FIG. 26.

Figure 27:
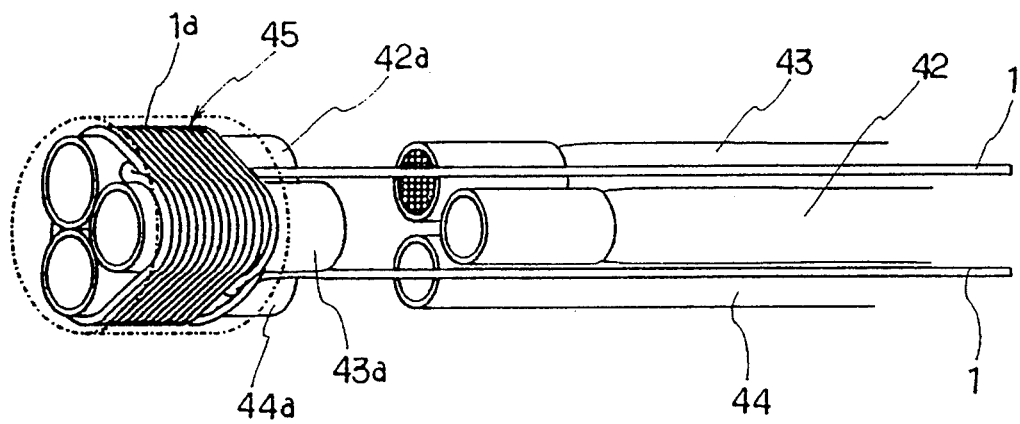
FIG. 27 is a perspective view showing the fifth version of the fourth embodiment of the invention.

FIG. 27 is a perspective view showing a further embodiment of the present invention. It is known in the art to use pipes 42a, 43a, 44a of metal/synthetic resin for fitting the distal ends of the diagnostic tools, e.g., an image guide 42, light guide 43, various other kinds of tubes 44 and the like. When applying the present invention to such construction, the distal ends of control wires 1 are spirally coiled up several times around the pipes 42a, 43a, 44a which are fixed to each other with adhesive and bundled up. By fitting and fixing the distal ends of the tools to the tubes 42a, 43a, 44a, a distal tip 45 of an endoscope is formed at the same time as the fixing of the distal ends of control wires 1. The openings formed on the outer surface can be sealed with adhesive or sealing parts, if necessary.

Further, when a precise positioning/spacing of the pipes is desired, a spacer element which has guide grooves for fitting each of the pipes may be put between them or molded together. This spacer can be used as the spacer element and as a sealing component.

Figure 28:
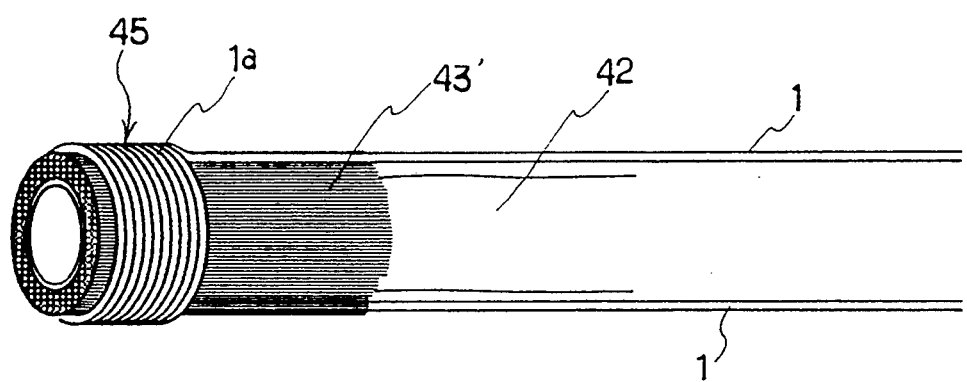
FIG. 28 is a perspective view showing the sixth version of the fourth embodiment of the invention.

In the embodiment shown in FIG. 28, the light guide 43 is positioned as covering the outer surface of the image guide 42. The outer surface of the light guide 43 is bundled up with or without adhesive, and control wires 1 are spirally coiled up several times around the end of the light guide 43. By unifying the spirally coiled portion 1a of the control wires 1 and the light guide 43, a distal tip 45 of an endoscope is formed at the same time as the distal ends of control wires 1 are secured. According to this structure of this embodiment, an endoscope with a very slender deflectable shaft can be provided.

Figure 29:
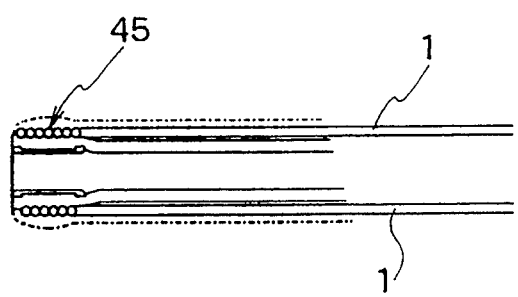
FIG. 29 is a partial cross-sectional side view showing the seventh version of the fourth embodiment of the invention.

The present invention has been described with reference to endoscopes, however, the construction of the present invention can also be used for catheters. As shown in FIG. 29, the distal ends of control wires 1 are spirally coiled up several times around the distal ends of the tube of the catheter. By unifying this spirally coiled portion of the control wires 1 and the distal ends of said tubes by molding, adhesive and the like, a distal tip 45 of the catheter is formed at the same time as the fixing of the distal ends of control wires 1.

In this manner, in the present invention, the distal tip of an endoscope can be formed at the same time as the distal ends of the control wires are fixed to the distal tip, simply by coiling up and fixing the distal ends of the control wires around a bundle of the distal ends of the image guide, a CCD, a light guide, various other kinds of diagnostic tools in the form of tubes and the like. Accordingly, the present invention can avoid the use of small and precise parts of metal/synthetic resin for the distal tip, and results in a slender distal tip for the endoscope, as well as simplifies the securing mechanism. Also, it can avoid thickening of the securing portion of the distal ends of the control wires, and slenderizes the shaft portion of the endoscope/catheter. That is particularly important in this apparatus.

Also, in the present invention, since the distal ends of the control wires are fixed to the distal tip of the endoscope/catheter within a certain area, the securing is sure and will not be broken even if the control wires are subject to strong tension or stress. Therefore, according to the present invention, it is possible to use thinner control wires, and the shaft portion of the endoscope/catheter can also be slenderized.

Furthermore, in the present invention, since the cylinder is simply fitted and fixed to the distal tip of the endoscope/catheter, no other parts are necessary. This simplifies the fixing of the control wires.

Still furthermore, in the present invention, it is possible to choose the method for fixing the control wires which avoids soldering. Therefore, according to the present invention, it is possible to use stainless steel wires which has not been possible to use before. The durability of these wires is improved over the prior art.

Figure 16:
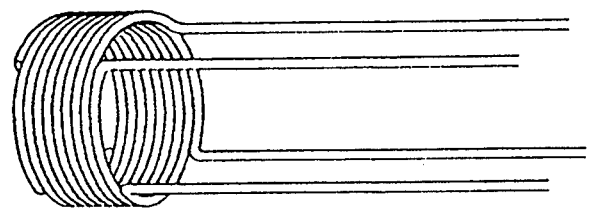
FIG. 16 is a perspective view showing yet another example of the spirally coiled portion of the control wires.

The above embodiments of the invention refer to two-directional controls; however, the construction of each of the embodiments are the same for four direction controls, as shown in FIG. 16.

What is claimed is:

1. An endoscope having a distal tip and a distal tip deflection control mechanism, the mechanism providing control to the distal tip by control wires having distal ends, the improvement characterized in that:
said distal ends of said control wires are spirally coiled to form a cylinder and said cylinder is fitted and secured about an end of said distal tip.

2. An endoscope as claimed in claim 1 wherein said end of said distal tip is the rear end.

3. An endoscope as claimed in claim 1 wherein said end of said distal tip is the front end.

4. An endoscope as claimed in claim 1 further comprising at least one tube having a distal end secured to said cylinder, wherein said at least one tube contains at least one from a group consisting of an image guide, a CCD, a light guide, and a diagnostic tool.

5. An endoscope as claimed in claim 4 wherein said distal ends of said plurality of tubes are secured to said cylinder by molding or adhesive.

6. An endoscope as claimed in claim 4 wherein said plurality of tubes are positioned in the distal end of the endoscope by a spacer body having a channel for each of said plurality of tubes.

7. An endoscope as claimed in claim 4 wherein said cylinder is provided with a set of longitudinal grooves and the distal ends of said plurality of tubes are secured within said grooves.

8. An endoscope having a distal tip, a distal tip deflection control mechanism, and at least one diagnostic tool from the group consisting of an image guide, a CCD, and a light guide, each of said at least one diagnostic tool having a distal operative end at said distal tip, said control mechanism providing control of said distal tip by control wires each having a distal end, the improvement characterized by the distal ends of said control wires being spirally wound into a cylinder and bundled about the distal operating end of said at least one diagnostic tool, wherein said distal ends of said control wires and said distal operative end of said at least one diagnostic tool are integrally formed.

9. An endoscope as claimed in claim 8 wherein said distal ends of said control wires and said distal operative end of said at least one diagnostic tool are held together by adhesive or molding.

10. An endoscope as claimed in claim 8 further comprising a spacer element for positioning the distal operative end of said at least one diagnostic tool with respect to one another.

11. An endoscope having a distal tip, a distal tip deflection control mechanism, and at least one diagnostic tool from the group consisting of an image guide, a CCD, and a light guide, each of said at least one diagnostic tool having a distal operative end and a tube formed for holding said distal operative end, said control mechanism providing control by control wires each having a distal end, the improvement characterized by the distal ends of said control wires being spirally wound around said at least one tube, wherein said at least one tube is integrally formed and the distal operative end of said at least one diagnostic tool is secured to said at least one tube.

* * * * *